(12) United States Patent
Hantash

(10) Patent No.: US 8,822,215 B2
(45) Date of Patent: Sep. 2, 2014

(54) DIFFERENTIATION OF MESENCHYMAL STEM CELLS INTO FIBROBLASTS, COMPOSITIONS COMPRISING MESENCHYMAL STEM CELL-DERIVED FIBROBLASTS, AND METHODS OF USING THE SAME

(71) Applicant: Escape Therapeutics, Inc., San Jose, CA (US)

(72) Inventor: Basil M. Hantash, East Palo Alto, CA (US)

(73) Assignee: Escape Therapeutics, Inc., East Palo Alto, CA (US)

( * ) Notice: Subject to any disclaimer, the term of this patent is extended or adjusted under 35 U.S.C. 154(b) by 0 days.

(21) Appl. No.: 13/725,472

(22) Filed: Dec. 21, 2012

(65) Prior Publication Data
US 2013/0122521 A1 May 16, 2013

Related U.S. Application Data

(62) Division of application No. 12/999,532, filed as application No. PCT/US2009/047647 on Jun. 17, 2009.

(60) Provisional application No. 61/074,547, filed on Jun. 20, 2008.

(51) Int. Cl.
*C12N 5/074* (2010.01)
*C12N 5/071* (2010.01)

(52) U.S. Cl.
CPC .......... *C12N 5/0656* (2013.01); *C12N 2501/11* (2013.01); *C12N 2501/115* (2013.01); *C12N 2501/15* (2013.01)
USPC ........................................ 435/325

(58) Field of Classification Search
CPC .. C12N 5/0652; C12N 5/0653; C12N 5/0656; C12N 5/0663; C12N 2501/11; C12N 2501/15
USPC ........................................ 424/93.7
See application file for complete search history.

(56) References Cited

U.S. PATENT DOCUMENTS

| 4,883,487 | A | 11/1989 | Yoshizato et al. |
| 5,196,190 | A | 3/1993 | Nangia et al. |
| RE35,399 | E | 12/1996 | Eisenberg |
| 5,658,331 | A | 8/1997 | Della Valle et al. |
| 5,693,332 | A | 12/1997 | Hansbrough |
| 5,906,937 | A | 5/1999 | Sugiyama et al. |
| 6,039,760 | A | 3/2000 | Eisenberg |
| 6,482,231 | B1 | 11/2002 | Abatangelo et al. |
| 6,846,675 | B2 | 1/2005 | Conrad et al. |
| 8,287,854 | B2 * | 10/2012 | Phan ............................ 424/93.2 |
| 2002/0111576 | A1 | 8/2002 | Greene et al. |
| 2003/0082152 | A1 | 5/2003 | Hedrick et al. |
| 2004/0009157 | A1 | 1/2004 | Gazit et al. |
| 2007/0212335 | A1 | 9/2007 | Hantash et al. |
| 2007/0225779 | A1 | 9/2007 | Hantash et al. |

FOREIGN PATENT DOCUMENTS

WO   WO 2007/046775   *   4/2007
WO   WO-2007046775 A1   4/2007

OTHER PUBLICATIONS

Lembach, Proc. Nat. Acad Sci USA, vol. 73, No. 1, p. 183-187, 1976.*
Zachariou, "TGFbeta1 ELISA System", Promega Notes Magazine, No. 55, 1996, p. 30.*
Zhao, Longmei, M.D., Ph.D., et al., "Transforming Growth Factor β1 Induces Osteogenic Differentiation of Murine Bone Marrow Stromal Cells," Tissue Engineering: Part A, Nov. 3, 2009, pp. 1-9, vol. 00, No. 00, Mary Ann Liebert, Inc.
Bonyadi et al. Mesenchymal Progenitor Self-Renewal Deficiency Leads to Age-Dependent Osteoporosis in Sca-1/Ly-6A Null Mice. Proc Nat Acad Sci. May 13, 2003, vol. 100, No. 10, pp. 5840-5845.
Buhring, et al., "Novel Markers for the Prospective Isolation of Human MSC", Ann. N.Y. Acad. Sci., 1106:262-271 (2007).
Covas et al. "Multipotent Mesenchymal Stromal Cells Obtained from Diverse Human Tissues Share Functional Properties and Gene-Expression Profile with CD146+ Perivascular Cells and Fibroblasts." Exp. Hematol. May 2008 (Epub Mar. 4, 2008), vol. 36, No. 5. pp. 642-654.
Cowan, et al., "Bone Morphogenetic Progein 2 and Retinoic Acid Accelerate in vivo Bone Formation, Osteoclast Recruitment, and Bone Turnover", Tissue Engineering, 11(3/4):645-658 (2005).
Fujimura, et al., "Neural Differentiation of Adipose-Derived Stem Cells Isolated from GFP Transgenic Mice", Biochemical and Biophysical Research Communications, 33:116-121 (2005).
Fukuda, "Development of Regenerative Cardiomyocytes from Mesenchymal Stem Cells for Cardiovascular Tissue Engineering", Artifical Organs, 25(3):187-193 (2001).
Gang, et al., "Skeletal Myogenic Differentiation of Mesenchymal Stem Cells Isolated from Human Umbilical Cord Blood", Stem Cells, 22:617-624 (2004).
Gronthos, et al., "Surface Protein Characterization of Human Adipose Tissue-Derived Stromal Cell", Journal of Cellular Physiology, 189:54-63 (2001).
Hata, et al., "A CCAAT/Enhancer Binding Protein beta Isoform, Liver-Enriched Inhibitory Protein, Regulates Commitment of Osteoblasts and Adipocytes", Molecular and Cellular Biology, 25(5):1971-1979, (2005), 10 pages.
International Search Report and Written Opinion for International Application No. PCT/US09/47647 mailed Aug. 16, 2009. 8 pages.
Ishii et al. "Molecular Markers Distinguish Bone Marrow Mesenchymal Stem Cells from Fibroblasts." Biochem Biophys Res Commun. Jun. 24, 2005, vol. 332, No. 1, pp. 297-303.

(Continued)

*Primary Examiner* — Ruth Davis
(74) *Attorney, Agent, or Firm* — Wilmer Cutler Pickering Hale and Dorr LLP

(57) ABSTRACT

Methods and compositions are provided for the differentiation and characterization of mammalian fibroblast from mesenchymal stem cells. The methods of the invention provide a means to obtain mesenchymal stem cell-derived fibroblast populations, e.g., seeded on a scaffold, which may be used in wound healing.

7 Claims, 11 Drawing Sheets

(56) References Cited

OTHER PUBLICATIONS

Liechty, et al., "Human Mesenchymal Stem Cells Engraft and Demonstrate Site-Specific Differentiation after in utero Transplantation in Sheep", Nature Medicine, 6(11):1282-1286 (2000).
Myers, et al., "Transplantation of Keratinocytes in the Treatment of Wounds", American Journal of Surgery, 170:75-83 (1995).
Okada et al. "Early Role of FSP1 in the Epithelial-mesenchymal Transformation." Am J Physiol. Oct. 1997. vol. 273, No. 4 Pt. 2, pp. 563-574.
Peister, et al., "Stable Transfection of MSCs by Electroporation", Gene Therapy, 11:224-228 (2004).
Piester, et al., "Adulst Stem Cells from Bone Marrow (MSCs) Isolated from Different Strains of Inbred Mice Vary in Surface Epitopes, Rates of Proliferation, and Differentiation Potential", Blood, 103(5):1662-1662 (2004).
Pittenger, et al., "Multilineage Potential of Adult Human Mesenchymal Stem Cells", Science, 284:143-147 (1999).
Simmons, et al., "Isolation, Characterization and Functional Activity of Human Marrow Stromal Progenitors in Hemopoiesis", Advances in Bown Marrow Purging and Processing: Fourth International Symposium, Wiley-Liss, Inc., pp. 271-280 (1994).
Strutz et al. "Identification and Characterization of a Fibroblast Marker:FSPI." J. Cell Biol. Jul. 1995. vol. 130, No. 2. pp. 393-405.
Tondreau, et al., "Mesenchymal Stem Cells Derived from CD133-Positive Cells in Mobilized Peripheral Blood and Cord Blood: Proliferation, Oct4 Expression, and Plasticity", Stem Cells, 23:1105-1112 (2005).
Williams, et al., "In Vitro Chrondogenesis of Bone Marrow-Derived Mesenchymal Stem Cells in Photopolymerizing Hydrogel", Tissue Engineering, 9(4):679-688 (2003).
Zuk, et al., "Human Adipose Tissue is a Source of Multipotent Stem Cells", Molecular Biology of the Cell, 13:4279-4295 (2002).
Heiss, Alexander et al. "Hierarchical Role of Fetuin-A and Acidic Serum Proteins in the Formation and Stabilization of Calcium Phosphate Particles." The Journal of Biological Chemistry. vol. 283, No. 21, May 23, 2008. pp. 14815-14825. 11 pages.
Iscove, N.N. et al. "Complete Replacement of Serum by Albumin, Transferrin, and Soybean Lipid in Cultures of Lipopolysaccharide-Reactive B Lymphocytes: The Journal of Experimental Medicine." vol. 147, Mar. 1, 1978. pp. 923-933. 11 pages.
Koi, Hideki et al. "Effects of Matrix Proteins and Heparin-Binding Components in Fetal Bovine Serum Upon the Proliferation of Ectoplacental Cone Cells in Mouse Blastocysts Cultured In Vitro." Biology of Reproduction. 52, No Month Listed, 1995. pp. 759-770. 12 pages.
Romijn, Herms J. "Development and Advantages of Serum-Free, Chemically Defined Nutrient Media for Culturing of Nerve Tissue." Biology of the Cell. Elsevier, Paris. 63, Sep. 5, 1988. pp. 263-268. 6 pages.
Spiro, Robert G. "Studies on Fetuin, a Glycoprotein of Fetal Serum." The Journal of Biological Chemistry. vol. 235, No. 10, Oct. 1960. pp. 2860-2869. 10 pages.
Lembach, Kenneth J. ":Induction of Human Fibroblast Proliferation by Epidermal Growth Factor (EGF): Enhancement by an EGF-binding Arginine Esterase and by Ascorbate." Proc. Nat. Acad. Sci. USA. vol. 73, No. 1. Jan. 1976. pp. 183-187.
Zachariou, Constantina Maragos. "TGFbeta1 Elisa System." Promega Notes Magazine. No. 55. No Month Listed. 1996. 3 pages.
Takahashi, Kazutoshi, et al., "Induction of Pluripotent Stem Cells from Adult Human Fibroblasts by Defined Factors," *Cell*, Nov. 30, 2007, pp. 861-872, vol. 131, Elsevier Inc.
Takahashi, Kazutoshi, et al., "Induction of Pluripotent Stem Cells from Mouse Embryonic and Adult Fibroblast Cultures by Defined Factors," *Cell*, Aug. 25, 2006, pp. 663-676, vol. 126, Elsevier Inc.
Park, In-Hyun, et al., "Reprogramming of Human Somatic Cells to Pluripotency with Defined Factors," *Nature*, Jan. 10, 2008, pp. 141-147, vol. 451, Nature Publishing Group.

* cited by examiner

DIFFERENTIATION OF MESENCHYMAL STEM CELLS INTO FIBROBLASTS, COMPOSITIONS COMPRISING MESENCHYMAL STEM CELL-DERIVED FIBROBLASTS, AND METHODS OF USING THE SAME

This application is a divisional of U.S. patent application Ser. No. 12/999,532 which is a National Phase Application under 35 U.S.C. §371 of International Patent Application No. PCT/US09/47647 filed Jun. 17, 2009, which claims the benefit of and priority to U.S. provisional patent application Ser. No. 61/074,547 filed Jun. 20, 2008, the disclosure of all of which is hereby incorporated by reference in its entirety for all purposes.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described herein.

BACKGROUND OF THE INVENTION

Each year, over 1.5 million skin wounds are due to burns and over 1 million skin wounds are due to skin cancer. Each year, skin wounds result in about 75,000 inpatient cases and 12,000 deaths, and in 2005, about $3.3 billion dollars were spend on wound care.

In the body, skin wound healing involves fibroblast secretion of a provisional matrix, a process that usually begins 7 days post-injury. However, the currently available tissue engineered skin substitutes are decellularized human skin, such as alloderm, which are used for humans in cases of chronic skin wounds (e.g., due to diabetes, vasculitis, malnutrition, infection), acute skin wounds (e.g., burns, skin cancer), skin malformation, etc. Such decellularized skin substitutes lack adnexal structures (e.g., sebaceous glands, hair follicles, melanocytes), a rete ridge pattern at the epidermal-dermal junction, and other vital living components that promote wound healing. Furthermore, high risk of infection remains in heterologous transplantation of the currently available skin substitutes.

Since the regeneration of both dermal and epidermal skin layers are critical for successful wound healing with limited scar formation and infection, new models are needed that are "true" skin substitutes.

SUMMARY OF THE INVENTION

Skin wound healing by the human body involves fibroblast secretion of a provisional matrix, which may begin seven days post-injury. Although fibroblasts are normally present in the dermis, the delay in activity suggests that stem cells that differentiate into fibroblasts may be recruited to the wound site.

Described herein is the differentiation of mesenchymal stem cells ("MSCs") into fibroblasts, which may be used in treating skin wounds. Accordingly, described herein are methods to differentiate stem cells of mesenchymal origin into fibroblasts. In this context, a scaffold may be utilized that allows for optimal migration of fibroblasts during wound healing. This method may be used to create tissue engineered skin substitutes for use in patients suffering from acute or chronic wounds such as burn victims or diabetic ulcers and the like.

In addition, a number of studies have shown that decreased collagen synthesis and increased degeneration contribute to skin aging. This has been attributed to the decreased activity of aging fibroblasts. Recent advances have led to the availability of collagen replacements products. Although aesthetic surgeons commonly employ these dermal fillers to volumize aging skin, the benefits are short-lived, lasting only 3 to 6 months. In contrast, the skin substitute described herein (e.g., mesenchymal stem cell-derived fibroblasts and a scaffold) allows for delivery of a stem cell source of fibroblasts into the dermis for a permanent and natural augmentation. This application may also be used in aesthetic reconstruction for breast cancer surgery and for surgical scar revision.

A method described herein differentiates a population of mesenchymal stem cells into fibroblasts by culturing a population of mesenchymal stem cells in fibroblast differentiating media (FDM). In one embodiment, fibroblast differentiating media comprises an epidermal growth factor receptor (EGFR) agonist and a transforming growth factor beta receptor (TGF-βR) agonist. In one embodiment, FDM as described herein comprises EGF and at least one member of the transforming growth factor beta (TGF-β) family. As a nonlimiting example, in one embodiment, FDM as described herein comprises EGF and TGF-β1. In another embodiment, FDM as described herein comprises EGF and TGF-β3. In another embodiment, with respect to growth factors or cytokines, the FDM consists of an EGFR agonist and a TGF-βR agonist. In one embodiment, with respect to growth factors or cytokines, the FDM consists of only EGF and EGF and TGF-β1.

In one embodiment, FDM as described herein comprises from about 1 pg/ml to about 1 µg/ml EGF and from about 1 pg/ml to about 1 µg/ml TGF-β. In another embodiment, FDM comprises from about 100 pg/ml to about 30 ng/ml EGF and from about 100 pg/ml to about 30 ng/ml TGF-β. In another embodiment, FDM comprises about 10 ng/ml EGF and about 10 ng/ml TGF-β.

In one embodiment, a fibroblast differentiating media further comprises L-glutamine (e.g., about 2 mM), fetal calf serum (0-10%), horse serum (0-10%), and antibiotics such as penicillin/streptromycin (100 units/ml). In one embodiment, FDM may contain 0-1% fetal calf serum and 0-1% horse serum.

In another embodiment, FDM as described herein is free of non-human serum (e.g., fetal calf serum, horse serum, etc.). In one embodiment, FDM that is free of non-human serum further comprises appropriate and well-known substitutes for non-human serum. Nonlimiting examples of substitutes for non-human serum include albumin, insulin, transferrin, progesterone, and other nutrients derived from non-animal sources (i.e., recombinant proteins made in *E. Coli*, or from humans, etc.).

An ordinarily skilled artisan will recognize the many sources of mesenchymal stem cells. In one embodiment, mesenchymal stem cells may be isolated from bone marrow. For example, the bone marrow stroma contains mesenchymal stem cells (also called marrow stromal cells in this context). Because MSCs can encompass multipotent cells derived from non-marrow tissues, including adult muscle, dental pulp, and fat tissue for example, the art sometime refers to MSCs as multipotent stromal cells. Thus, in another embodiment, mesenchymal stem cells may be isolated from adipose tissue.

In another embodiment, mesenchymal stem cells are isolated are enriched using well-known methods, e.g., cell sorting by flow cytometry ("FACS"; fluorescence activated cell sorter) with an antibody directed toward a mesenchymal stem cell marker, e.g., Sca-1), etc.

In another embodiment, mesenchymal stem cells are cultured, e.g., for expansion (e.g., proliferation), prior to differentiation into fibroblasts. An exemplary mesenchymal stem cell proliferation media (MSCPM) may be Iscove's Modified Dulbeccos Media plus Glutamax (2 mM), fetal calf serum (0-10%), horse serum (0-10%), and antibiotics such as pen/strep (100 units/ml). In addition, bFGF (0-100 ng/ml) may be added to the media in lieu of fetal calf serum or horse serum when animal free media is desired.

Accordingly, provided herein are compositions comprising mesenchymal stem cell-derived fibroblasts, e.g., mammalian mesenchymal stem cell-derived fibroblasts, which may be identified for example by having increased expression of fibroblast markers, such as the fibroblast-specific marker FSP-1, and additionally collagen, such as types III and XV.

Also described herein are methods of making and using skin substitutes, e.g., compositions comprising mesenchymal stem cell-derived fibroblasts. In one embodiment, a skin substitute described herein comprises mesenchymal stem cell-derived fibroblasts on top of or within a scaffold. Nonlimiting examples of scaffolds include hydrogel, PLGA, collagen gel, matrigel, spongastan, and fibronectin. In one embodiment, the scaffold is hydrogel (puramatrix 1%).

Methods of making skin substitutes are also described. In one embodiment, a population of mesenchymal stem cells are isolated, placed (e.g., seeded) on top of or within a scaffold, and differentiated into fibroblasts by culturing the population and scaffold in fibroblast differentiation media. In another embodiment, the population of mesenchymal stem cells is expanded by culture of the population and scaffold with mesenchymal stem cell proliferation media prior to differentiation into fibroblasts.

In another embodiment, after differentiation of mesenchymal stem cells into fibroblast on top of or within a scaffold, the skin substitute may be exposed to epidermal stem cells, e.g., isolated from a hair bulge. The epidermal stem cells may be expanded and differentiated into keratinocytes using well-known methods, and may give rise to hair follicles, melanocytes, sebaceous glands, an entire epidermal keratinocyte layer, etc. Exposure of mesenchymal stem cell-derived fibroblasts on top of or within a scaffold to epidermal stem cells, and the subsequent expansion and differentiation of epidermal stem cells into keratinocytes, provides another skin substitute as described herein.

Also provided are methods of using skin substitutes as described herein for acute or chronic wounds and burn applications, aesthetic skin rejuvenation, post-surgical reconstruction, and scar revision. Skin substitutes as described herein may be used corneal injuries, mucosal injuries (e.g., urethra, oral mucosa, other mucosal surfaces), to replace non-pigmented skin (e.g., vitiligo) with pigmented skin, to replace non hair bearing skin (alopecia) with hair bearing skin, etc.

The methods of differentiating mesenchymal stem cells into fibroblasts, making skin substitutes with such mesenchymal stem cell-derived fibroblast and a scaffold, and using such skin substitutes in wound care provide several advantages over the art. For example, skin substitutes described herein may provide living components that promote wound healing, a permanent source of additional youthful fibroblasts, and a natural and permanent source of new collagen synthesis. Skin substitutes as described herein may also replace scar prone fibroblasts with fibroblasts that heal without scarring, and methods of using of autologous stem cell transplantation to generate a skin substitute that may avoid immune rejection issues as well as risks of infection.

DETAILED DESCRIPTION OF THE INVENTION

Figure 1A:
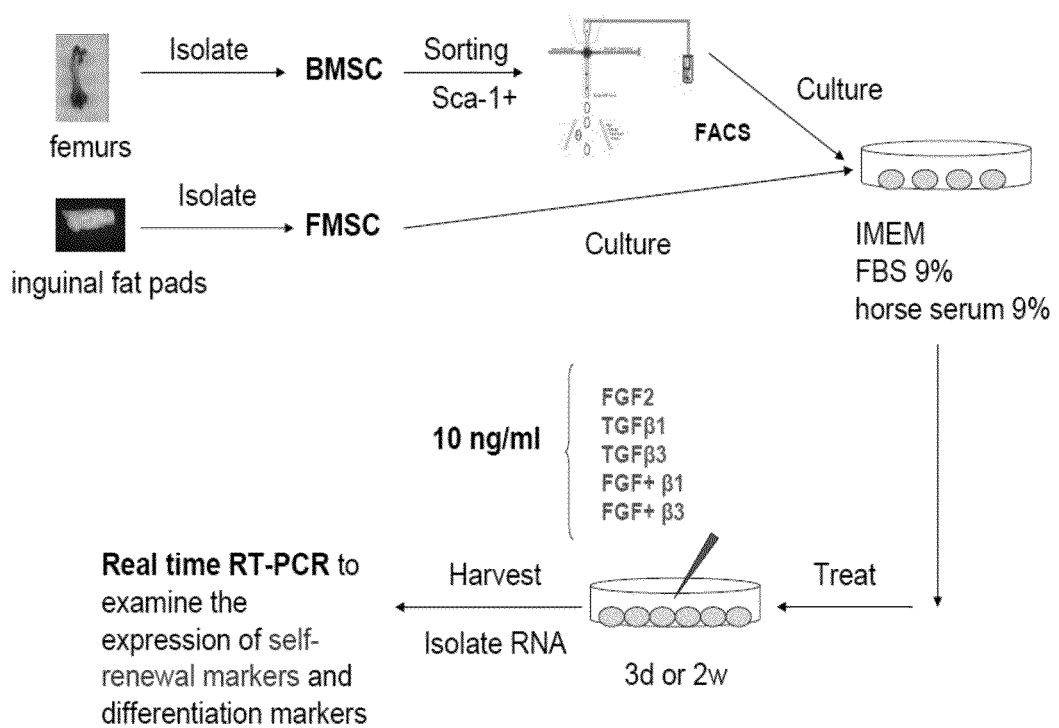
FIGS. 1A and 1B provide schematic representations of exemplary methods of differentiating mesenchymal stem cells isolated from bone marrow or adipose tissue (e.g., by FACS and/or culture) into fibroblasts and confirming such differentiating and isolation.
Figure 1B:
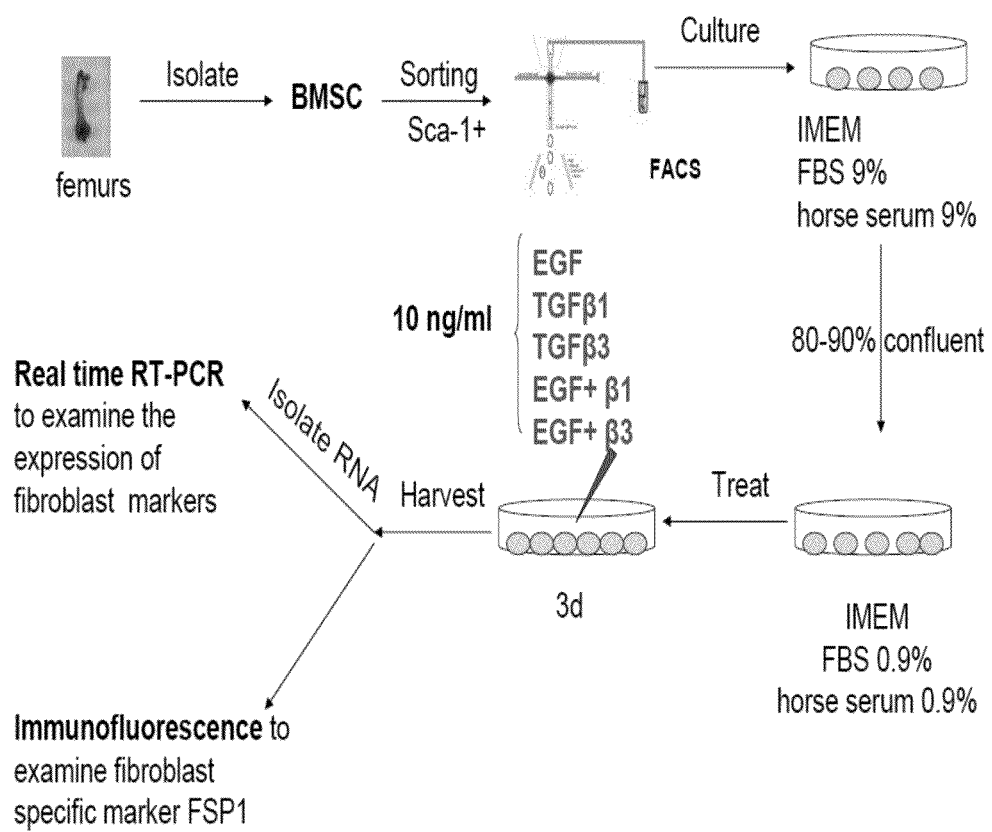

Described herein are methods of differentiating mesenchymal stem cells into fibroblasts, compositions comprising such mesenchymal stem cell-derived fibroblasts, and methods of using such compositions.

Mesenchymal Stem Cell (MSC). As used herein, the term MSC refers to a cell capable of giving rise to differentiated cells in multiple mesenchymal lineages, specifically to osteoblasts, adipocytes, myoblasts, chondroblasts, and as described herein, fibroblasts. Generally, mesenchymal stem cells also have one or more of the following properties: an ability to undergo asynchronous, or asymmetric replication, that is where the two daughter cells after division can have different phenotypes; extensive self-renewal capacity; and clonal regeneration of the tissue in which they exist, for example, the non-hematopoietic cells of bone marrow. "Progenitor cells" differ from stem cells in that they typically do not have the extensive self-renewal capacity.

MSCs have been harvested from the supportive stroma of a variety of tissues. For example, in both mouse and human, a candidate population of cells has been identified in subcutaneous adipose tissue (AMSC). These cells have demonstrated the same in vitro differentiation capacity as BM-MSC (bone marrow mesenchymal stem cells; bone marrow is also a source for MSCs herein) for the mesenchymal lineages, osteoblasts, chondrocytes, myocytes, neurons, and adipocytes (Zuk et al. (2002) *Mol. Biol. Cell,* 13, 4279-95; Fujimura et al. (2005) *Biochem. Biophys. Res. Commun,* 333, 116-21). Additionally, cell surface antigen profiling of these cells has revealed similar cell surface marker characteristics as the more widely studied BM-MSC (Simmons et al. (1994) *Prog. Clin. Biol. Res.* 389, 271-80; and Gronthos et al. (2001) *J. Cell Physiol.* 189, 54-63).

MSC may be characterized by both the presence of cell surface markers associated with specific epitopes identified by antibodies and the absence of certain cell surface markers as identified by the lack of binding of specific antibodies. MSC may also be identified by functional assays both in vitro and in vivo, particularly assays relating to the ability of stem cells to give rise to multiple differentiated progeny; assays for responsiveness to canonical WNT signaling; and the like.

The cells of interest are typically mammalian, where the term refers to any animal classified as a mammal, including humans, domestic and farm animals, and zoo, laboratory, sports, or pet animals, such as dogs, horses, cats, cows, mice, rats, rabbits, etc. Preferably, the mammal is human.

The MSC which are employed may be fresh, frozen, or have been subject to prior culture. They may be fetal, neonate, or adult. MSC may be obtained from adipose tissue (see U.S. Patent application 20030082152); bone marrow (Pittenger et al. (1999) Science 284(5411):143-147; Liechty et al. (2000) Nature Medicine 6:1282-1286); G-CSF or GM-CSF mobilized peripheral blood (Tondreau et al. (2005) *Stem Cells* 23(8): 1105-1112), or any other conventional source. Generally, mesenchymal stem cells may be isolated using protocols familiar to one of ordinary skilled in the art.

As a non-limiting example, bone marrow derived MSC may be separated from hematopoietic cells by plating isolated cells on treated polystyrene tissue culture dishes. This allows MSC to attach, while the hematopoietic cells remain suspension, floating in the dish. The isolation media may be aspirated between 0 to 24 hours later, and immediately replaced with fresh isolation media. The cells may be serially passaged 2 more times to ensure complete removal of any contaminating cells such as hematopoietic cells. Just prior to reaching confluence, cells may be subcultured by first washing cells with a sterile solution, e.g., phosphate-buffered saline (PBS), followed by the addition of a solution comprising trypsin, e.g., TrypLE Select™, which may be an animal free product. Such subculturing allows maintenance of MSC in culture for at least 10-20 passages. Other similar methods of isolating MSC, e.g., from adipose tissue or from any other tissue that contains MSC, are also well-known in the art.

In one embodiment, MSC may be isolated by fluorescence activated cell sorting (FACS) using well-known methods. As a non-limiting example, bone marrow derived cells may be stained with an antibody specific for an MSC marker, and separated on the basis of expression of that marker. In one embodiment, MSC may be isolated from other cells by staining with Sca1.

Isolation of MSC may be confirmed by well-known methods, e.g., analysis of MSC marker expression and/or proliferation. Analysis of MSC markers may be performed using well-known methods (e.g., flow cytometric analysis, Western blot analysis, RT-PCR, in situ hybridization, immunoflourescence, immunohistochemistry, etc). Analysis of MSC proliferation may be performed using well-known methods, e.g., BrdU incorporation. Non-limiting examples of MSC markers that may be used to confirm isolation of MSC by FACS, or other similar methods, include Sca1, ABCG2, Sox9, Activin, Oct4, Bmi1, Hand1, IGF2, MTS1, Col1, Col3, Col15, Col18, Prolyl hydroxylase, and Stella.

Non-differentiating culture conditions. MSC as described above may be propagated continuously in culture, using culture conditions that promote proliferation without promoting differentiation, using methods known in the art. The cells can be maintained in medium, e.g. DMEM; RPMI; etc. in the presence of fetal bovine serum or serum-free replacement without differentiation. Generally the cells may be passaged at about 75 to 95% confluence, using a protease, e.g. trypsin, collagenase, etc. In one embodiment, MSC are propagated continuously in mesenchymal stem cell proliferation media, e.g., IMDM plus L-glutmaine (e.g., at a concentration of about 2 mM), fetal calf serum (e.g., at a concentration of about 0-10%), horse serum (e.g., at a concentration of about 0-10%), and antibiotics such as penicillin/streptomycin (pen/strep; e.g., at a concentration of about 100 units/ml). In embodiments where fetal calf serum and/or horse serum may be undesirable, e.g., in methods of treating humans, bFGF (e.g., at about 0-100 ng/ml) may be used lieu of the fetal calf and/or horse serum.

Differentiating culture conditions. Differentiating cells are obtained by culturing or differentiating MSC in a growth environment that enriches for cells with the desired phenotype, e.g. osteoblasts, adipocytes, and as described herein, fibroblasts, etc. The culture may comprise agents that enhance differentiation to a specific lineage.

Osteogenic differentiation may be performed by plating cells and culturing to confluency, then culturing in medium comprising β-glycerol phosphate, ascorbic acid and retinoic acid (see Cowan et al. (2005) *Tissue engineering* 11, 645-658).

Adipogenic differentiation may be performed by plating cells and culturing to confluency, then culturing in medium comprising dexamethasone, indomethacin, 3-isobutyl-1-methylxanthine (IBMX), and insulin, then maintaining in growth media with insulin.

Myocyte differentiation may be performed by plating cells and culturing to confluency, then culturing in medium comprising horse serum, dexamethasone, and hydrocortisone (see Eun et al. (2004) *Stem Cells* 22:617-624); or 5-azacytidine (see Fukuda et al. (2001) *Artificial Organs* 25:187).

Chondrocyte differentiation may be performed by plating cells and culturing to confluency, then culturing in medium comprising dexamethasone, ascorbic acid 2-phosphate, insulin, transferrin, selenous acid, with or without TGF-β1 (see Williams et al. (2003) *Tissue Engineering* 9(4):679).

Differentiation and Characterization of MSC-Derived Fibroblast

As described herein, mesenchymal stem cells may be differentiated into fibroblasts by culturing MSCs in a fibroblast differentiating medium described herein, e.g., media with EGF plus TGF-β1 or EGF plus TGF-β3 (see, e.g., Example 3). Accordingly, provided herein are methods for differentiating mesenchymal stem cells into fibroblasts comprising culturing a population of mesenchymal stem cells in media comprising an EGFR agonist and a TGF-βR agonist.

Fibroblast. As used herein, fibroblast refers to a type of cell may synthesize and/or maintain the extracellular matrix of many animal tissues. Fibroblasts may also provide a stroma and may play a critical role in wound healing. Fibroblasts may maintain the structural integrity of connective tissues by continuously secreting precursors of the extracellular matrix, e.g., fibroblasts may be cells that synthesize collagen but do not produce bone, bone minerals, or cartilage. Fibroblast may also be cells that proliferate at a site of injury causing a scar, unlike cartilage or bone, neither of which scar. Fibroblasts may also be defined as having high expression of FSP-1, collagen III, and/or collagen type 15.

Epidermal Growth Factor (EGF). As used herein, epidermal growth factor or EGF is a growth factor, which is a 6 KDa protein with 53 amino acid residues and three intramolecular disulfide bonds. EGF acts by binding with high affinity to epidermal growth factor receptor (EGFR) on the cell surface and stimulating the intrinsic protein-tyrosine kinase activity of the receptor. The tyrosine kinase activity, in turn, initiates a signal transduction cascade that results in a variety of biochemical changes within the cell—a rise in intracellular calcium levels, increased glycolysis and protein synthesis, and increases in the expression of certain genes including the gene for EGFR—that ultimately lead to DNA synthesis and cell proliferation. An exemplary protein sequence for murine EGF is set forth as NCBI Accession No. NP_034243. An exemplary protein sequence for human EGF is set forth as NCBI Accission No. NP_001954.

Epidermal growth factor receptor (EGFR). As used herein, epidermal growth factor receptor (EGFR) refers to a cell-surface receptor for members of the epidermal growth factor family (EGF-family), e.g., EGF. Epidermal growth factor receptor may be a member of the ErbB family of receptors, a subfamily of four closely related receptor tyrosine kinases: EGFR (ErbB-1), HER2/c-neu (ErbB-2), Her 3 (ErbB-3) and Her 4 (ErbB-4). Upon binding of one of its specific ligands, (e.g., epidermal growth factor), EGFR may be activated and undergo a transition from an inactive monomeric form to an active homodimer—although there is some evidence that performed inactive dimers may also exist before ligand binding. In addition to forming homodimers after ligand binding, EGFR may pair with another member of the ErbB receptor family, such as ErbB2/Her2/neu, to create an activated heterodimer. EGFR dimerization stimulates its intrinsic intracellular protein-tyrosine kinase activity. As a result, autophosphorylation of several tyrosine (Y) residues in the C-terminal domain of EGFR occurs. These are Y845, Y992, Y1045, Y1068, Y1148 and Y1173. This autophosphorylation elicits downstream activation and signaling by several other proteins that associate with the phosphorylated tyrosines through their own phosphotyrosine-binding SH2 domains. These downstream signaling proteins initiate several signal transduction cascades, principally the MAPK, Akt and JNK pathways, leading to e.g., DNA synthesis and cell proliferation. Such proteins modulate phenotypes such as cell migration, adhesion, and proliferation. The kinase domain of EGFR can also cross-phosphorylate tyrosine residues of other receptors it is aggregated with, and can itself be activated in that manner. An exemplary protein sequence for murine EGFR is set forth as NCBI Accession No. NP_997538. An exemplary protein sequence for human EGF is set forth as NCBI Accission No. NP_005219.2.

Transforming growth factor beta (TGF-β). As used herein, transforming growth factor beta (TGF-β) refers to a protein, which may be secreted, and which exists in at least three isoforms: TGF-β1, TGF-β2 and TGF-β3. The TGF-β family is part of a superfamily of proteins known as the transforming growth factor beta superfamily, which includes inhibins, activin, anti-mullerian hormone, bone morphogenetic protein, decapentaplegic and Vg-1. The peptide structures of the three members of the TGF-β family are highly similar. They are all encoded as large protein precursors; TGF-β1 contains 390 amino acids and TGF-β2 and TGF-β3 each contain 412 amino acids. They each have an N-terminal signal peptide of 20-30 amino acids that they require for secretion from a cell, a pro-region (called latency associated peptide or LAP), and a 112-114 amino acid C-terminal region that becomes the mature TGF-β molecule following its release from the pro-region by proteolytic cleavage. The mature TGF-β protein dimerizes to produce a 25 KDa active molecule with many conserved structural motifs. TGF-β has nine cysteine residues that are conserved among its family; eight form disulfide bonds within the molecule to create a cysteine knot structure characteristic of the TGF-β superfamily while the ninth cysteine forms a bond with the ninth cysteine of another TGF-β molecule to produce the dimer. Many other conserved residues in TGF-β are thought to form secondary structure through hydrophobic interactions. The region between the fifth and sixth conserved cysteines houses the most divergent area of TGF-β molecules that is exposed at the surface of the molecule and is implicated in receptor binding and specificity of TGF-β. An exemplary protein sequence for murine TGF-β1 is set forth as NCBI Accession No. NP_035707. An exemplary protein sequence for murine TGF-β2 is set forth as NCBI Accession No. NP_033393. An exemplary protein sequence for murine TGF-β3 is set forth as NCBI Accession No. NP_033394. An exemplary protein sequence for human TGF-β1 is set forth as NCBI Accession No. NP_000651. An exemplary protein sequence for human TGF-β2 is set forth as NCBI Accession No. NP_003229. An exemplary protein sequence for human TGF-β3 is set forth as NCBI Accession No. NP_003230.

TGF-β receptor (TGF-βR). As used herein, TGF-β receptor refers to a serine/threonine kinase receptor that binds a member of the TGF-β family (e.g., TGF-β1, TGF-β2, TGF-β3, etc). Generally, a TGF βR may exist in several different isoforms, and may be homo- or heterodimeric. Three TGF-β receptor types may be distinguished by their structural and functional properties. Receptor types I and II (TGF-βRI and TGF-βRII, respectively) have a high affinity for TGF-β1 and low affinity for TGF-β2. TGF-β receptor type III has a high affinity for both TGF-β1 and TGF-β2. An exemplary protein sequence for murine TGF-βRI is set forth as NCBI Accession No. NP_033396. An exemplary protein sequence for murine TGF-βRII is set forth as NCBI Accession No. NP_083851. An exemplary protein sequence for human TGF-βRI is set forth as NCBI Accession No. NP_004603. An exemplary protein sequence for human TGF-βRII is set forth as NCBI Accession No. NP_001020018.1.

Fibroblast growth factor (FGF). As used herein, fibroblast growth factors are a family of growth factors involved in angiogenesis, wound healing, and embryonic development. The FGFs are heparin-binding proteins and interactions with cell-surface associated heparan sulfate proteoglycans have been shown to be essential for FGF signal transduction. FGFs are key-players in the processes of proliferation and differentiation of cells, particularly endothelial cells; they (especially FGF-1) promote angiogenesis. An exemplary protein sequence for murine FGF-1 is set forth as NCBI Accession No. NP_034327. An exemplary protein sequence for human FGF-1 isoform 1 precursor is set forth as NCBI Accession No. NP_000791.1.

Agonist. As used herein, an agonist is a molecule that activates the downstream biological effects of the cognates' interaction. For example, an agonist may act as a ligand (e.g., EGF, TGF-β, etc.) and bind the ligand's receptor (e.g., EGFR, TGF-βRI, TGF-βRII, etc.), which causes intracellular signaling via activating that receptor, which in turn effectuates the downstream biological effects of activating that receptor, such as but not limited to, cell activation, proliferation, differentiation, cytokine release, up-regulation of genes, cell-surface expression of proteins, and the like. Alternatively, an agonist may bind at a site that is adjacent to either of the cognate's respective binding sites and induce a conformational change in that cell protein, thereby enhancing its biological activity. For example, an agonist may bind to EGFR, but not block the binding between EGF and EGFR and cause a conformational change in EGFR such that the binding between EGF and EGFR is enhanced, such as by increased affinity or avidity between the binding pairs.

Therefore as used herein, an EGFR agonist or a TGF-βR agonist is a molecule that agonizes one or more of EGFR or TGF-βR biological activities, respectively. Exemplary EGFR agonists include antibodies (including scFv antibodies, diabodies, chimeric antibodies, humanized antibodies), peptidomimetics, small molecules, EGF and fragments thereof, etc., which agonize one or more EGFR biological activities (e.g., initiation of at least one signal transduction cascades (e.g., the MAPK, Akt and or JNK pathway), induction of MSC differentiation into fibroblasts, etc.). Exemplary TGF-βR agonists include antibodies (including scFv antibodies, diabodies, chimeric antibodies, humanized antibodies), peptidomimetics, small molecules, TGF-β and fragments thereof, etc., which agonize one or more TGF-βR biological activities (e.g., induction of MSC differentiation into fibroblasts, etc.).

Provided herein are methods of differentiating mesenchymal stem cells (MSC) into fibroblasts, the method comprising culturing a population of MSC in media comprising an EGFR agonist and a transforming growth factor beta receptor agonist. In one embodiment, the EGFR agonist is EGF. In another embodiment, the TGF-βR agonist is selected from the group consisting of transforming growth factor beta 1, transforming growth factor beta 2, and transforming growth factor beta 3. In another embodiment, the TGF-βR agonist is TGF-β1. In another embodiment, the TGF-βR agonist is TGF-β2. In another embodiment, the TGF-βR agonist is TGF-β3.

A population of MSC may be obtained by well-known methods, in addition to those described herein. In one embodiment, the isolation of a population of MSC comprises contacting a population of MSC with an antibody specific for Sca-1 for a period of time sufficient to bind said Sca-1 and selecting for cells expressing said Sca-1, e.g., by FACS. Other nonlimiting methods for such preparation of a population of MSC is to first select a population of cells expressing a marker identifying mesenchymal stem cells, for example, SH3 or SH2 by immunomagnetic selection of adipose tissue and/or a low density human bone marrow cell sample (see, e.g., Buhring et al. (2007) "Novel Markers for the Prospective Isolation of Human MSC" Ann. N.Y. Acad. Sci. 1106:262-271). Alternatively, it is contemplated that the initial cell selection can be based on the Sca-1 cell surface marker and may be optionally further characterized using monoclonal antibodies to other known MSC markers, which may include one or more of the MSC markers described herein (e.g., HLA-G, HLA-E+, INDO, CD200, CD47, CD271, CD140b, etc.).

In one embodiment, mesenchymal stem cells may be differentiated into fibroblasts by culture in media (e.g., Iscove's Modified Dulbecco's Media) comprising an EGFR agonist plus a TGF-βR agonist. The concentration of EGFR agonist and TGF-βR agonist for such differentiation of mesenchymal stem cells into fibroblasts may be readily determined by an ordinarily skilled artisan using well known methods, e.g., assays analyzing cell phenotype. In one embodiment, FDM comprises the EGFR agonist, EGF, and the TGF-βR agonist, TGF β, each at a concentration of about 1 ng/ml to about 20 ng/ml, e.g., about 5 ng/ml, about 10 ng/ml, about 20 ng/ml, etc. In another embodiment, mesenchymal stem cells may be differentiated by culture in an EGFR agonist and TGF βR agonist containing media, which may also contain L-glutamine, fetal calf serum, horse serum and antibiotics such as pen/strep (100 units/ml). As described herein, such media may be referred to as fibroblast differentiating media (FDM) for the purpose of this disclosure. In one embodiment, FDM may contain 0-1% fetal calf serum and 0-1% horse serum. In another embodiment, FDM as described herein is free of non-human serum (e.g., fetal calf serum, horse serum, etc.). In one embodiment, FDM that is free of non-human serum further comprises appropriate and well-known substitutes for non-human serum. Nonlimiting examples of substitutes for non-human serum include albumin, insulin, transferrin, progesterone, and other nutrients derived from non-animal sources (i.e., recombinant proteins made in *E. Coli*, or from humans).

As described herein, mesenchymal stem cells may begin to differentiate into fibroblasts after at least 1 day in FDM. Analysis or separation of fibroblasts by cell staining for fibroblast markers, e.g., fibroblast specific protein 1 (FSP-1), expression of collagen III, expression of collagen type 15, etc., may use conventional methods, as known in the art. Techniques providing accurate enumeration include confocal microscopy, fluorescence microscopy, fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g., propidium iodide).

The affinity reagents may be specific receptors or ligands for the cell surface molecules indicated above. In addition to antibody reagents, polynucleotide probes specific for an mRNA of interest (e.g., collagen III, collagen type 15, etc); peptide ligands and receptor; effector and receptor molecules, and the like, may be used. Antibodies may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

Of particular interest is the use of antibodies as affinity reagents. Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each cell surface marker.

The antibodies may be added to MSC-derived fibroblasts, and incubated for a period of time sufficient to bind the available antigens. The incubation may generally be at least about 5 minutes and generally less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium that maintains the viability of the cells. A preferred medium is phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc.

The compositions described herein comprise MSC-derived fibroblasts, which may be at or about 10 or 25% of the cell population, more usually at least about 40% of the cell population, preferably at least about 50% of the cell composition, still more preferably at least about 75% of the cell composition, and most preferably at least about 90% or more. The desired cells are identified by their surface phenotype, by the ability to self-renew, etc. The enriched cell population may be used immediately, or may be frozen at liquid nitrogen temperatures and stored for long periods of time, being thawed and capable of being reused. The cells will usually be stored in 10% DMSO, 50% FCS, 40% RPMI 1640 medium. The population of cells enriched for the MSC may be used in a variety of screening assays and cultures, as described below.

The MSC-derived fibroblasts can be substantially purified from differentiation cultures by standard sorting technology. For example, the differentiated fibroblasts can be sorted on the basis of expression of fibroblast specific markers, such as one or more of FSP-1, collagen type III, and/or collagen type XV. The substantially purified population can then be used, for example, to populate scaffolds as described infra.

MSC-derived fibroblasts may be maintained and/or expanded in vitro under various culture conditions. Culture medium may be liquid or semi-solid, e.g. containing agar, methylcellulose, etc. The cell population may be conveniently suspended in an appropriate nutrient medium, such as Iscove's modified DMEM or RPMI 1640, normally supplemented with fetal calf serum (about 5-10%), L-glutamine, a thiol, particularly 2-mercaptoethanol, and antibiotics, e.g. penicillin and streptomycin.

Mesenchymal Stem Cell-Derived Fibroblast Compositions and Uses Thereof

Accordingly, provided herein are compositions comprising mesenchymal stem cell-derived fibroblasts, e.g., mammalian mesenchymal stem cell-derived fibroblasts, which may express a fibroblast marker, e.g., FSP-1. As used herein "mesenchymal stem cell-derived fibroblast" refers to a fibroblast differentiated from a mesenchymal stem cell, wherein said differentiation involves at least some ex vivo manipulation. Examples of differentiation involving some ex vivo manipulation include, but are not limiting to, isolation of mesenchymal stem cells, ex vivo culture of mesenchymal stem cells (e.g., in mesenchymal stem cell proliferation media and/or fibroblast differentiating media), ex vivo culture of mesenchymal stem cell-derived fibroblasts, manipulation of an in vivo microenvironment (e.g., via injection of mesenchymal stem cells, mesenchymal stem cell-derived fibroblast, an EGFR agonist (e.g., EGF), a TGF-βR agonist (e.g.,TGF-β), etc), and the like.

Also described herein are therapeutic compositions comprising mesenchymal stem cell-derived fibroblasts, e.g., mesenchymal stem cell-derived fibroblasts on top of or within a scaffold, and methods of using such compositions, e.g., as a skin substitute. In one embodiment, mesenchymal stem cells are seeded on or within a scaffold and subsequently induced to differentiate into fibroblasts.

Exemplary scaffolds for use in compositions described herein include, but are not limited to, hydrogel (puramatrix 1%), PLGA, collagen gel, matrigel, fibronectin, and other scaffold materials familiar to an ordinarily skilled artisan. In one embodiment, the scaffold is hydrogel.

Methods of making compositions comprising mesenchymal stem cell-derived fibroblasts on top of or within a scaffold are also described herein. In one embodiment, mesenchymal stem cells and a scaffold, e.g., a hydrogel mixture (e.g., puramatrix 1%) may be plated onto a polystyrene culture dish and exposed to mesenchymal stem cell proliferation media (MSCPM), e.g., proliferation media containing IMDM plus Glutamax (2 mM), fetal calf serum (0-10%), horse serum (0-10%), and antibiotics such as pen/strep (100 units/ml). In another embodiment, bFGF (0-100 ng/ml) may be added to the media in lieu of fetal calf serum or horse serum when animal free media is desired.

After expansion of mesenchymal stem cells with MSCPM in the scaffold of choice, the mixture may be treated with FDM to induce differentiation of the mesenchymal stem cells into fibroblasts. After successful differentiation into fibroblasts, the skin substitute (scaffold plus mesenchymal stem cell-derived fibroblasts) may be exposed to epidermal stem cells, preferably isolated from the hair bulge via methods known to an ordinarily skilled artisan. Hair bulge stem cells may be expanded and then differentiated into keratinocytes using well-known methods. Hair bulge stem cells give rise to hair follicles, melanocytes, sebaceous glands, as well as the entire epidermal keratinocyte layer. Compositions comprising a scaffold, mesenchymal stem cell-derived fibroblasts, and epidermal skin cells (which may be differentiated into keratinocytes) may also be used as a skin substitute in methods of wound healing as described herein.

An ordinarily skilled artisan will recognize that a skin substitute as described herein may comprise additional skin components. Non-limiting examples of additional skin components that may be included in a skin substitute include hair stem cells, melanocytes, etc. (see, e.g., U.S. Patent Application Publication Nos. 20070225779 and 20070212335, each of which are incorporated in its entirety by reference).

In one embodiment, non mesenchymal stem cells that are capable of differentiating into fibroblasts such as epithelial derived stem cells may also be used to populate the scaffold. Dermal Papilla stem cells may be used to generate hair follicle structures. Neural crest stem cells or melanocyte stem cells may be used to generate melanocytes.

In one embodiment, MSC-derived fibroblasts as described herein (including compositions comprising the same (e.g., skin substitutes)) are used in methods in the treatment of scars, burns, medical diseases of pathologic fibroblasts (e.g., sclerodermal, renal failure (e.g., due to fibrosis), as collagen producing dermal fillers, etc. The use of autografts and allografts for the treatment of burns and wound closure is described in Myers et al., A. J. Surg. 170(1):75-83 (1995) and U.S. Pat. Nos. 5,693,332; 5,658,331; and 6,039,760, each of which is incorporated herein by reference. Additional skin substitutes finding potential use in the present invention include, e.g., U.S. Pat. Nos. 6,846,675; 5,196,190; 6,482,231 and RE 35,399. Accordingly, the present invention provides methods for wound closure, including wounds caused by burns, comprising treating the patient in need of wound closure with a skin substitute as described herein under conditions such that the wound is closed. In another embodiment, a method of treating a scar, burn, scleroderma or renal failure may comprise replacing scar prone fibroblasts with MSC-derived fibroblasts as described herein. Similarly, a method of providing collagen to a subject comprises injecting at least one MSC-derived fibroblast into skin of the subject. In another embodiment, the method of providing collagen comprises injecting a composition comprising a mesenchymal stem cell, EGF and TGF-β into skin of the subject. In another embodiment, a method of treating a subject comprises injecting a therapeutic composition comprising EGF and TGF-β, wherein said therapeutic composition induces differentiation of cells (e.g., mesenchymal stem cells), into fibroblasts.

EXAMPLES OF THE INVENTION

For all statistical analysis in the Examples, all data represent a minimum of 3 independent experiments. Means±SEM were calculated using Microsoft Excel and statistical significance was determined using a paired analysis of variance. P values are shown in the figure legends and were taken to be statistically significant at p<0.05.

All citations are expressly incorporated herein in their entirety by reference.

Example 1

Isolation and Culture of Murine Bone Marrow-derived Mesenchymal Stem Cells

Mesenchymal stem cells (MSC) from mouse bone marrow were isolated according to Peister et al (Peister, Mellad et al. 2004). Briefly, three-week old female and male BALB/c mice were individually euthanized using CO2. The femurs and tibiae were removed, cleaned of all connective tissue, and placed on ice in 2 mL of complete isolation media (CIM) that consisted of α-MEM supplemented with 20% fetal bovine serum (FBS; Atlanta Biologicals, Atlanta, Ga.), 100 U/mL penicillin, 100 µg/mL streptomycin, and 12 µM L-glutamine. All media and supplements were purchased from Invitrogen (Carlsbad, Calif.) unless otherwise specified. The ends of each tibia and femur were clipped to expose the marrow, flushed out using a 20 gauge needle, and centrifuged for 1 minute at 1200 rpm. The pellet was resuspended in 1 mL CIM with a micropipette. The cells from 2 mice were plated in 10 mL CIM in a 100 mm culture dish.

After 24 hours, nonadherent cells were removed by washing with phosphate-buffered saline (PBS) and 10 mL fresh CIM was added. The adherent cells (passage 0) were washed, and media changed with fresh CIM every 3 days. After 1 week, the cells were washed with PBS and detached by incubation in 1 mL 0.25% trypsin/1 mM ethylenediaminetetraacetic acid (EDTA) for 2 minutes at 37° C. The cells that did not lift off in 2 minutes were discarded. The trypsin was neutralized by the addition of 5 mL CIM, and all the cells (passage 1) from one dish were replated in 10 mL CIM in a 100 mm culture dish. The CIM was replaced every 3 days. At passage 2, cells were expanded by plating at 50 cells/cm2 in complete expansion media (CEM) consisting of Iscove modified Dulbecco medium supplemented with 9% FBS, 9% Horse serum, 100 U/mL penicillin, 100 µg/mL streptomycin, and 12 µM L-glutamine. The CEM was replaced every 3 to 4 days and serially passaged.

Example 2

Confirmation of Mesenchymal Stem Cell Phenotype

Expression of Mesenchymal Cell Markers

In contrast to progenitor cells, multipotent stem cells lack contact inhibition. It was noted that isolated bone marrow derived MSC that were Sca1 positive lacked contact inhibition when cultured (data not shown).

Isolated MSC were analyzed by for expression of MSC markers. As determined by RT-PCR, mesenchymal stem cells expressed surface markers such as Sca1 and ABCG2 (data not shown). As determined by RT-PCR, mesenchymal stem cells also expressed Sox9, Activin, Oct4, Bmi1, Hand1, IGF2, MTS1, Col1, Col3, Col15, Col18, Prolyl hydroxylase, Stella, but expressed low levels of or were negative for Bcl2, UTF1, Nanog, Tert, Ecadherin, and Keratin5 (data not shown). Mesenchymal stem cells do not express SSEA1, SSEA3, or SSEA4 as determined by RT-PCR (data not shown).

Figure 2:
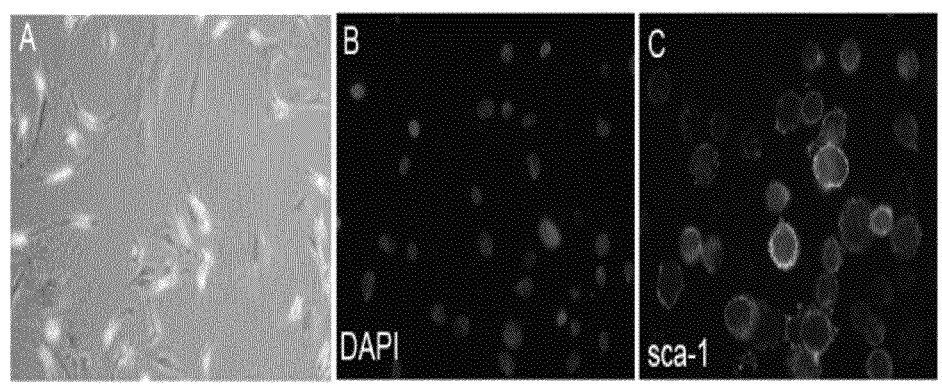
FIG. 2 shows staining of bone marrow derived mesenchymal cells with no antibody (Panel A), DAPI (Panel B), and anti-Sca1 antibody (C) are shown. Images with no primary antibody, and no primary antibody and DAPI show no specific staining (data not shown).

Mesenchymal stem cell isolated from adult murine femur bone marrow at passage 5 were attached to a tissue culture plate 24 hours after seeding (FIG. 2A). BMSCs were harvested with 0.25% trypsin/EDTA and washed with cold PBS once. Cells were incubated in 100 µL 1° antibody diluted in PBS containing 3% bovine serum albumin (BSA) solution (1:500 dilution) for 1 hour at room temperature. Sca-1 and FSP-1 1° and all 2° antibodies were purchased from abcam (Cambridge, Mass.). Cells were then centrifuged at 800 rpm for 5 min and washed once with cold PBS. Sequentially, cells were incubated in 100 µL FITC-labeled 2° antibody solution at a dilution of 1:100 in PBS containing 3% BSA for 30 min at room temperature in the dark. After washing with cold PBS, cells were suspended in 20 µL cold PBS and smeared on the slides and allowed to air dry. The slides were treated with anti-fade mounting medium plus DAPI (Vector Laboratories, Burlingame, Calif.) and observed under fluorescent microcopy (Leica CTR6500, Leica Microsystems, Bannockburn, Ill.). DAPI was used to stain the nucleus of all bone marrow derived MSC (FIG. 2B), and anti-Sca1 antibody was used to stain the same cells (FIG. 2C). As shown in FIG. 2C, staining with anti-Sca1-antibody was consistent with a membrane pattern, which is the expected location of Sca-1.

Proliferation of Adipose-Derived Mesenchymal Stem Cells

Figure 3:
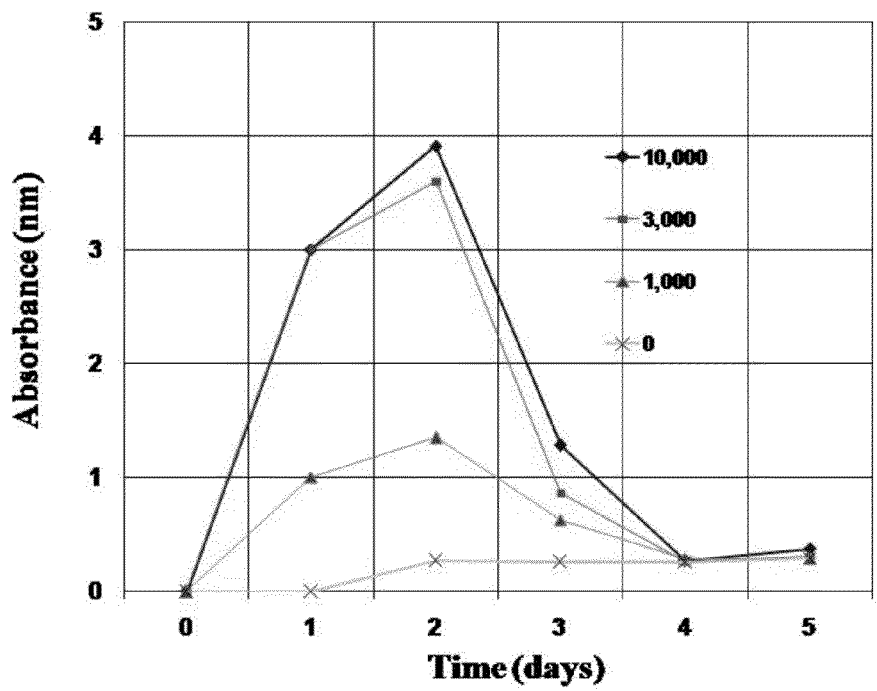
FIG. 3 shows proliferation of adipose-derived mesenchymal stem cells seeded at 0 (x), $1 \times 10^3$ (▲), $3 \times 10^3$ (■) or $1 \times 10^4$ (♦) cells represented by BrdU incorporation (Absorbance (nm); y-axis) over a period of time (days; x-axis).

Adipose-derived MSC were seeded in triplicate for each time point at 0, $1\times10^3$, $3\times10^3$ or $1\times10^4$ cells per well of a 96-well plate and incubated with BrdU according to the manufacturer's protocol (Roche Applied Biosciences, Indianapolis, Ind.). One, 2, 3, 4 and 5 days later, BrdU incorporation was determined As demonstrated in FIG. 3, the growth rate of adipose-derived MSC peaked at day two, indicating that the isolated cells were multipotent self-renewing MSC rather than differentiated cells.

Osteogenic and Adipogenic Differentiation of Bone Marrow Derived Mesenchymal Stem Cells Bone marrow derived mesenchymal stem cells were freshly isolated from the femurs of mice, FACS sorted using an anti-Sca1 antibody, and cultured to induce osteogenic or adipogenic differentiation. Osteogenic or adipogenic differentiation of MSC isolated from bone marrow was induced by culturing cells in osteogenic or adipogenic differentiation media (OS-medium or AD-medium, respectively, Cell Applications, Inc. CA) for 7 days according to the manufacturer's instructions.

Figure 4:
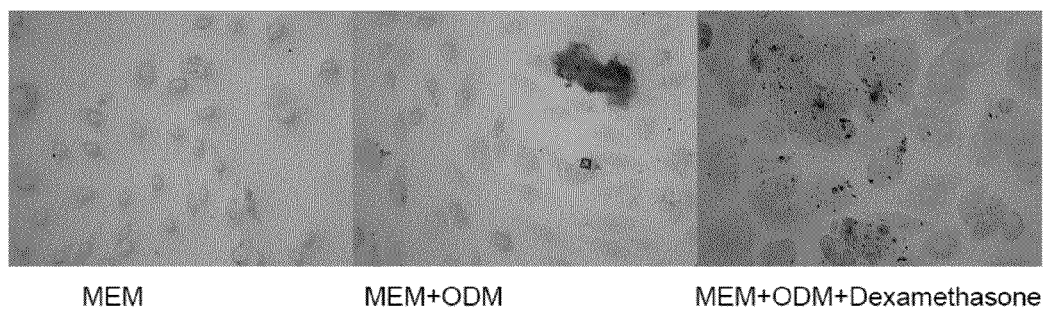
FIG. 4 shows the results of alkaline phosphatase staining of bone marrow derived mesenchymal stem cells that have been cultured in MEM media alone, MEM media plus osteogenic differentiation media (MEM+ODM), or MEM media plus osteogenic differentiation media and dexamethasone (MEM+ODM+Dexamethasone).

Formation of mineralization nodules after osteogenic induction was assessed by staining with alizarin red S (AR-S, Sigma, San Louis, Ind.) according to the modified protocol of Salasznyk et al 2006. Cells were rinsed in PBS and incubated with 40 mM AR-S (pH 4.2) with rotation for 10 min, then rinsed 5 times with water followed by a 15 min wash with PBS with rotation to reduce nonspecific AR-S staining. The stained nodules were visualized using a light field microscope. As shown in FIG. 4, mesenchymal cells derived from bone marrow as described herein differentiate into osteoblasts in OS medium.

Alkaline Phosphatase (ALP) staining was used to detect bone mineralization. After culturing BMSCs for 14 days with or without cytokines the media was aspirated and cells stained with ALP (StemTAG, Cell Biolabs, Inc. CA) according to the manufacturer's protocol. Briefly, after washing twice with PBS, cells were fixed with fixing solution for 2 min, then washed again with PBS and incubated with StemTAG ALP staining solution for 30 min in the dark. ALP staining solution was aspirated and cells were then washed with PBS and observed under light microscopy.

ALP activity was assessed via a colorimetric assay of enzyme activity using an ALP kit (Cell Biolab, Inc. San Diego, Calif.), following the manufacturer' instructions. Briefly, cell layers were washed 3 times with PBS, then total proteins extracted using the Protein Extract Reagents kit (Pierce, Rockford, Ill.), followed by centrifugation to remove cellular debris. Fifty µL of lysate was then mixed with 50 µL of the freshly prepared colorimetric substrate para-nitrophenyl phosphate, and incubated at 37° C. for 30 min. The enzymatic reaction was stopped by adding 50 µL of 0.2 N NaOH. The optical density of the yellow product para-nitrophenol was determined by a HTS 7000 Plus Bio Assay reader (Perkim ELmer, Waltham, Mass.) at 405 nm. Protein concentration of the cell lysates was measured with a BCA Protein Assay Kit (Pierce, Rockford, Ill.) and ALP activity was then expressed as nmol N-PPN/min/mg of protein. The results indicate that over 80% of bone marrow derived mesenchymal cells cultured in OS-medium are alkaline phosphatase positive.

Adipo-Red and red oil staining was used to confirm BMSC adipogenic differentiation. AdipoRed staining was performed according to the manufacturer's protocol (BioE, St. Paul, Minn.). As determined by Adipo-Red staining, mesenchymal stem cells isolated from bone marrow as described herein differentiate into adipocytes when cultured in AD medium (FIG. 5).

To stain with oil red O, cells were washed with PBS and fixed with 10% formalin for 20 min. Cells were then washed twice with PBS and once with 60% isopropyl alcohol, and stained with Oil red O solution (Sigma-Aldrich, St. Louis, Mo.) for 15 min. The cells were washed with PBS once and observed through a light field microscope (Hata et al 2005).

Figure 6:
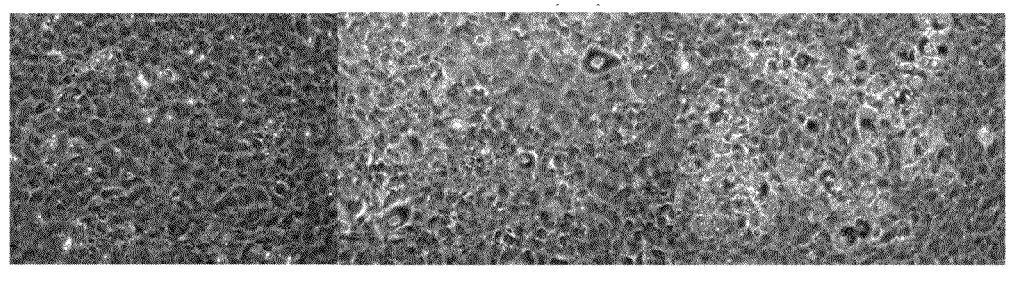
FIG. 6 shows the results of Oil red O staining of murine 3T3 cells (3T3), murine 3W cells (3W), and bone marrow derived mesenchymal stem cells that have been cultured in adipogenic differentiation media (MSC).

Neither murine 3T3 nor 3W cells were stained with Oil red O (FIG. 6). In contrast, mesenchymal stem cells isolated from bone marrow as described herein differentiated into adipocytes when cultured in AD-medium for 7 days as determined by Oil red O staining (FIG. 6).

Figure 5:
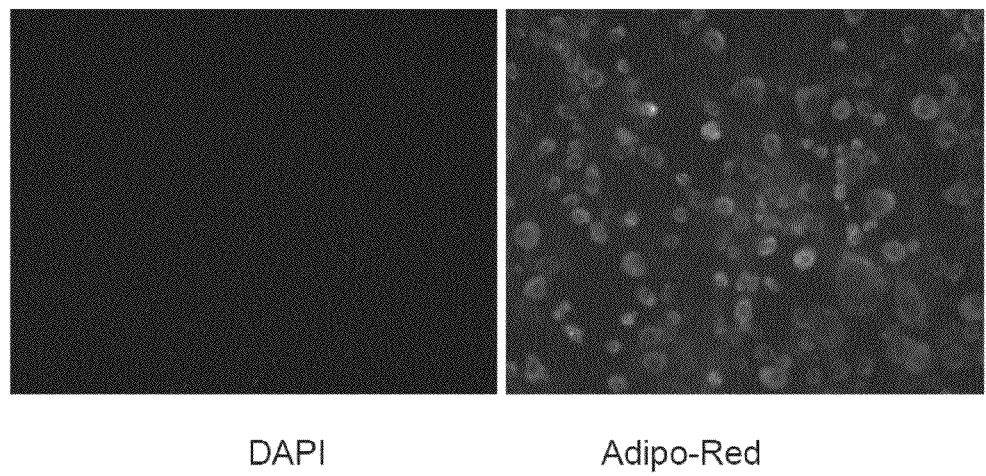
FIG. 5 shows the results of DAPI or Adipo-Red staining of bone marrow derived mesenchymal stem cells that have been cultured in adipogenic differentiation media.

The data represented in FIGS. 4-6 demonstrate that the MSCs isolated as described herein undergo osteogenic differentiation or adipogenic differentiation in the presence of osteogenic induction medium or adipogenic induction medium, respectively. Accordingly, MSCs isolated as described herein exhibit stem cell characteristics, e.g., multipotency, and not already fibroblasts, but instead require differentiation through a defined media.

Example 3

Fibroblast Differentiation

Fibroblast differentiation

At passage 5 or 6, BMSCs were placed in 60 mm culture dishes at a density of $2.5\times10^5$ cells/well in CEM. When cells reached 80-90% confluence, the cells were cultured in fibroblast differentiating media, e.g., the media was supplemented with 10 ng/mL of cytokines (TGF-β1, bFGF, and/or EGF; PeproTech Inc, Rocky Hill, N.J.) for 3 or 14 days. Media was changed and cytokines were replenished every other day. The media can be, for example, IMDM media with low serum (0.9% FBS, 0.9% horse serum) with 10 ng/mL of TGF-β1, bFGF, and/or EGF, or just with 10 ng/mL of TGF-β1 and EGF.

Characterization of Mesenchymal Stem Cell-Derived Fibroblasts by Real-Time RT-PCR Total RNA was isolated after 14 days using TRIzol (Invitrogen, Carlsbad, Calif.). RNA was dissolved in ddH2O and stored at −80° C. The yield of RNA was determined by measuring absorbance at 260 nm using a spectrophotometer (Thermo Fisher Scientific, Inc. Waltham, Mass.). Reverse transcriptase (RT) reactions were annealed at 24° C. for 10 min, followed by first-strand cDNA synthesis at 48° C. for 1 hr and heat inactivation at 95° C. for 5 min. The resulting cDNA was stored at −20° C. until assayed by real-time PCR.

Real-time PCR analysis was performed using SYBR Green PCR core reagents (Applied Biosystems, Foster City, Calif.) following the manufacturer's protocol on an ABI Prism 7700 Sequence Detection System (Applied Biosystems, Inc. Foster City, Calif.). All primers were designed using the Primer3 program (Whitehead Institute, Cambridge, Mass.). Primers were directed to Nanos3, Oct-4, Abcg2, Collagen III, Collagen XV, Bmi1, and Stella.

Briefly, the real-time PCR reactions were performed with 14 µL each of SYBR Green master mix and forward and reverse primers. Six µL of cDNA sample diluted 10-fold from the RT reaction was added to the final reaction mixture. The 384-well real time PCR format included six 2-fold dilutions in triplicate of the plasmid DNA standards. The wells of the plate were sealed with optical adhesive covers (Bio-Rad Laboratories, Hercules, Calif.) and centrifuged at low speed (300×g) for 5 min to ensure complete mixing. Each sample was analyzed at least in triplicate.

The PCR protocols involved activation of DNA polymerase followed by 40 cycles of denaturation at 94° C. for 15 s, and annealing and extension at 60° C. for 1 min. The PCR threshold cycle number (CT) for each sample was calculated at the point where the fluorescence exceeded the threshold limit. The threshold limit was fixed along the linear logarithmic phase of the fluorescence curves at 10 to 20 standard deviations (SDs) above the average background fluorescence. Relative expression levels were calculated using the standard curve method recommended by Applied Biosystems.

Table 1 shows that expression of the self-renewal markers Oct-4, ABCG2, Nanos3, Stella, and Bmi-1 by BMSC cultured in FDM. As shown in Table 1, culture of BMSC with TGF β1 and EGF downregulated markers of self-renewal, suggesting that the BMSC were induced to differentiate.

| Self-renewal Markers | TGF-b1/EGF | TGF-b3/EGF | FGF | FGF + b1 | FGF + b3 |
|---|---|---|---|---|---|
| Oct-4 | ↓ | ↓↓ | ↑ | ↓ | ↓ |
| ABCG2 | ↓ | ↓ | ↑ | ↓ | ↓ |
| Nanos3 | ↓ | ↓ | ↑ | ↓ | ↓ |
| Stella | ↓ | ↓↓ | ↑ | ↓ | ↓ |
| Bmi-1 | ↓ | ↓ | — | ↓ | ↓ |

Figure 7:
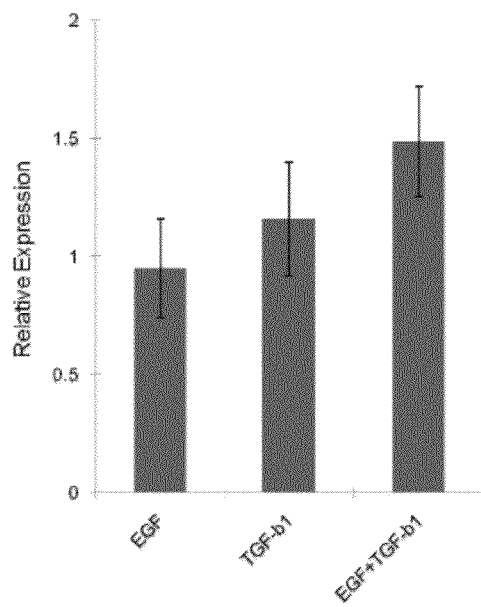
FIG. 7 is the relative expression of collagen III (y-axis) by bone marrow mesenchymal stem cells cultured for two weeks in EGF only (EGF; x-axis), TGF-β1 only (TGF b1; x-axis), or a cockatil of EGF and TGF-β1 (EGF+TGF-b1; x-axis).

BMSC were grown in CEM supplemented with 10 ng/ml EGF only, 10 ng/ml TGF-β1 only, or 10 ng/ml EGF+10 ng/ml TGF-β1. After two weeks, RNA was isolated and expression of collagen III was determined by real-time RT-PCR. As shown in FIG. 7, EGF modulates TGF-β1 induced differentiation of BMSC into fibroblasts. The expression of collagen 3 was increased in BMSCs grown in CEM supplemented with the cocktail of 10 ng/ml EGF+10 ng/ml TGF-β1 (FIG. 7).

Figure 8:
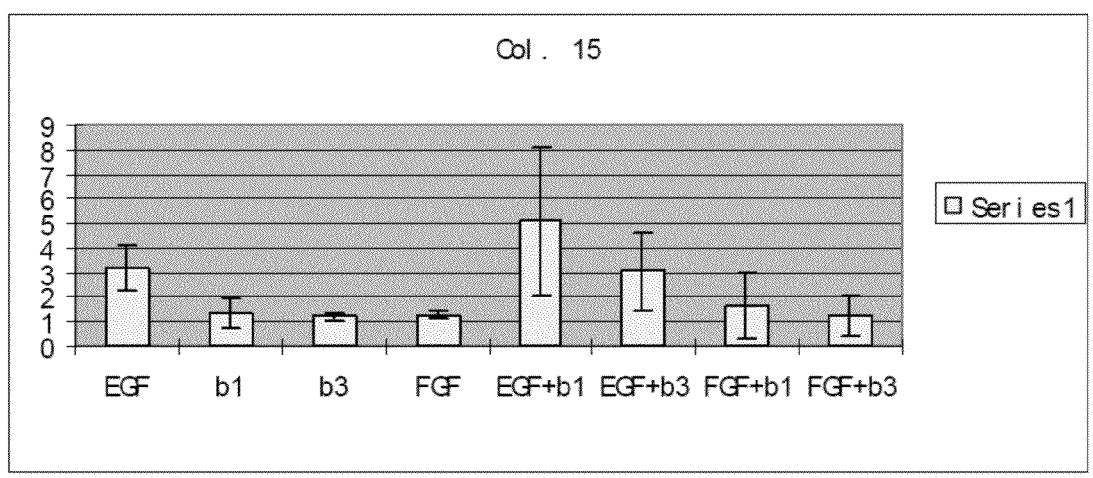
FIG. 8 is the relative expression of Collagen type 15 (y-axis) by bone marrow mesenchymal stem cells cultured for two weeks in 10 ng/ml EGF (EGF; x-axis), 10 ng/ml TGF β1 (b1; x-axis); 10 ng/ml TGF-β3 (b3; x-axis), 10 ng/ml FGF (FGF; x-axis); 10 ng/ml EGF plus 10 ng/ml TGF-β1 (EGF+b1); 10 ng/ml EGF plus 10 ng/ml TGF-β3 (EGF+b3); 10 ng/ml FGF plus 10 ng/ml TGF-β1 (FGF+b1); or 10 ng/ml FGF+10 ng/ml TGF-β3 (FGF+b3).
Figure 9:
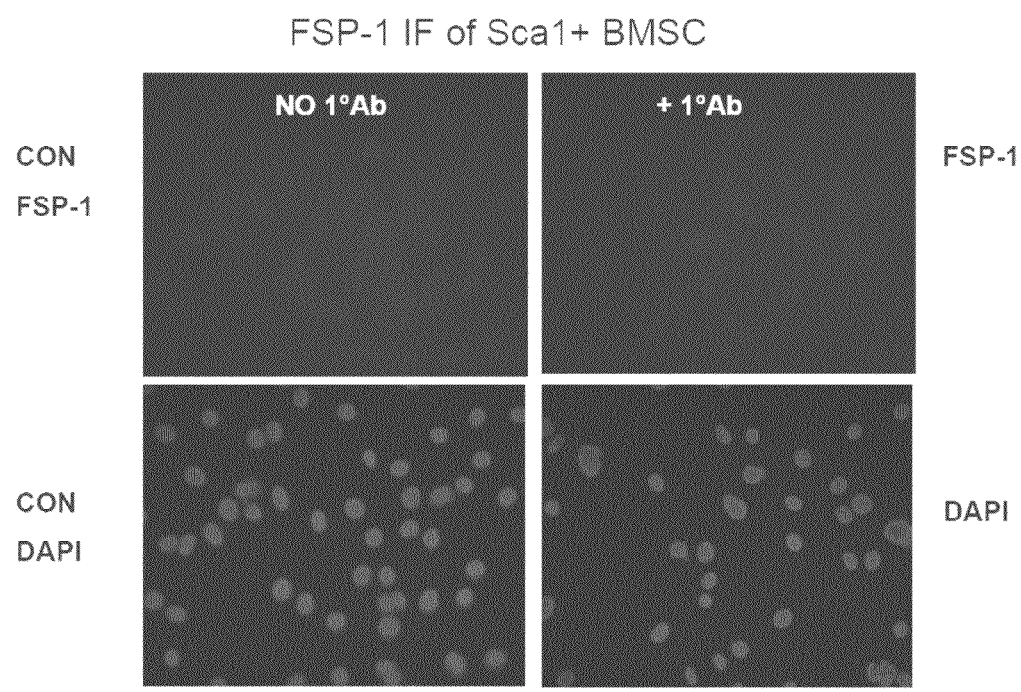
FIG. 9 shows the results of immunofluorescence staining of Sca1+ bone marrow derived mesenchymal stem cells prior to culture in fibroblast differentiating media using FSP-1 or DAPI detection antibodies in the absence of primary antibody (NO 1° Ab; CON FSP-1 or CON DAPI) or presence of primary antibody (+1° Ab; FSP-1 or DAPI).
Figure 10:
FIG. 10 shows the results of FSP-1 immunofluorescence staining of Sca1+ bone marrow derived mesenchymal stem cells grown in the presence of EGF+TGF-β1, EGF alone, or TGF-β1 alone.
Figure 11:
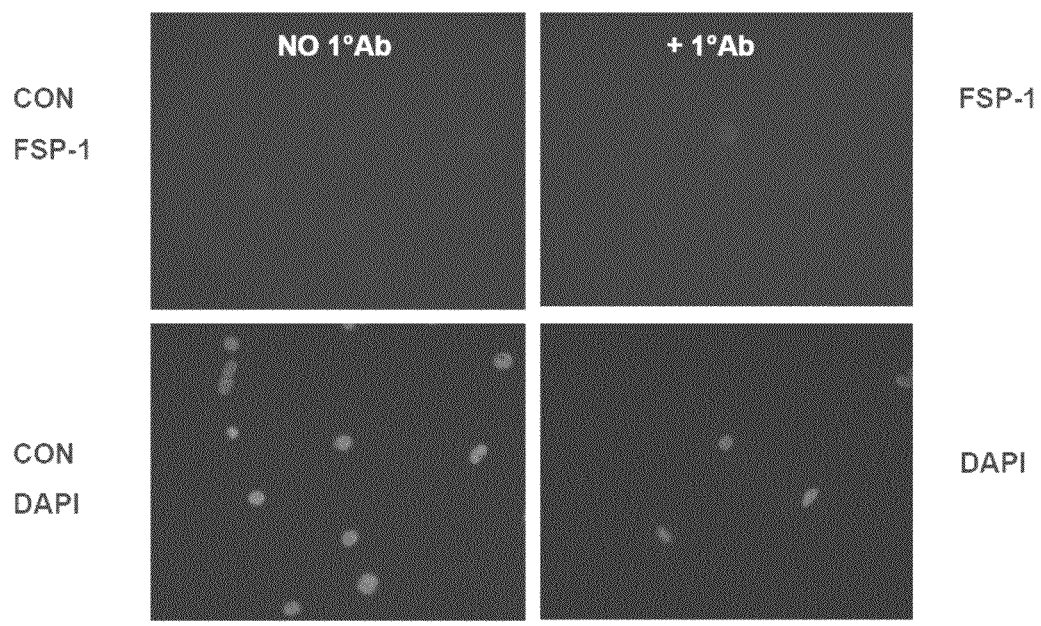
FIG. 11 shows the results of immunofluorescence staining of keratinocytes using FSP-1 or DAPI detection antibodies in the absence of primary antibody (No 1° Ab; CON FSP-1 or CON DAPI) or presence of primary antibody (+1° Ab; FSP-1 or DAPI).

BMSC were grown in CEM supplemented with 10 ng/ml EGF, 10 ng/ml TGF-β1, 10 ng/ml TGF-β3, 10 ng/ml FGF, 10 ng/ml EGF plus 10 ng/ml TGF-β1, 10 ng/ml EGF plus 10 ng/ml TGF-β3, 10 ng/ml FGF plus 10 ng/ml TGF-β1, or 10 ng/ml FGF+10 ng/ml TGF-β3. After two weeks, RNA was isolated and expression of collagen type 15 was determined by real-time RT-PCR. As shown in FIG. 8, EGF plus TGF-β3 promoted BMSC differentiation into fibroblasts as determined by collagen type 15 expression. Furthermore, optimal induction of collagen type 15 expression was detected by BMSCs treated with the cocktail of EGF plus TGF-β1.

Figure 15:
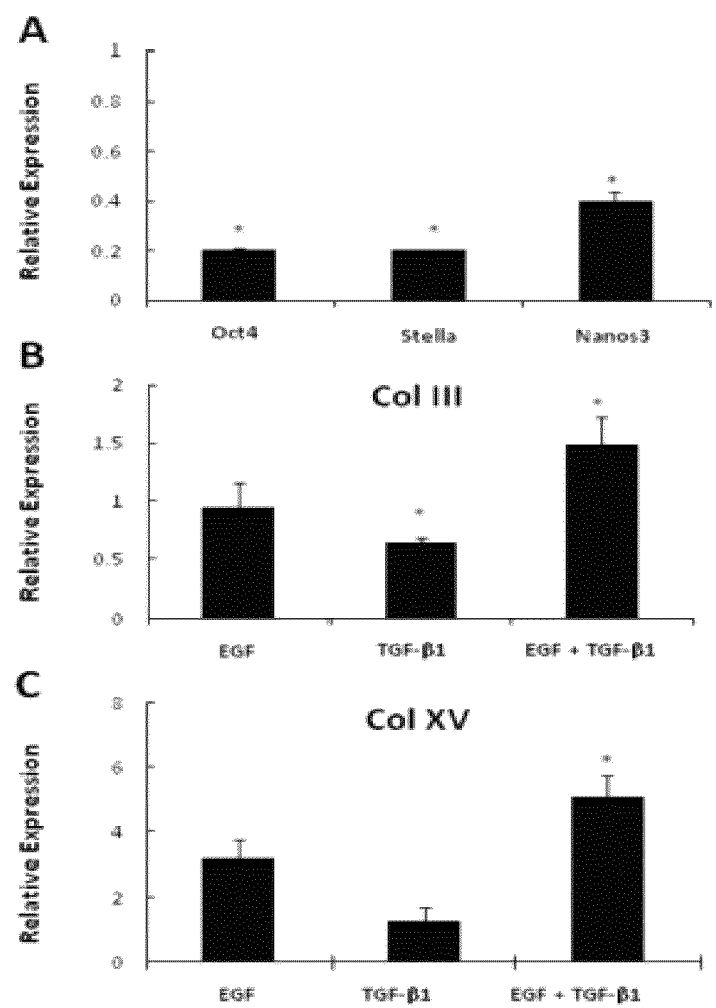
FIG. 15 shows that EGF modulates TGF-β1 induced differentiation. Murine BMSCs were cultured in IMDM with EGF (10 ng/mL), TGF-β1 (10 ng/mL), or EGF (10 ng/mL) plus TGF-β1 (10 ng/mL) for 14 days. RNA was collected from cells and real-time PCR was conducted to determine the expression levels of stem cell markers (Panel A), collagen III (Panel B), and collagen XV (Panel 15C). y-axis refers to expression levels normalized to untreated samples. *p<0.05, compared to EGF or TGF-β1 group.

Real-time PCR on additional experiments confirm that Oct-4, Nanos3, and STella expression was decreased to 0.2±0.01, 0.4±0.04, and 0.2±0.00-fold, respectively in cells exposed to EGF plus TGF-β1 (FIG. 15A). The expression levels of fibroblasts markers collagen XV and III were enhanced, confirming the earlier experiments: 5.1±0.7 and 1.5±0.2-fold in cells exposed to EGF plus TGF-β1 (FIG. 15B and FIG. 15C). The expression of collagen III was not upregulated in BMSCs treated with EGF (0.9±0.2-fold) or TGF-β1 (0.6±0.0-fold) alone (FIG. 15B.)

Characterization of Mesenchymal Stem Cell-Derived Fibroblasts by Immunostaining

BMSCs or BMSC cultured in FDM as described above were harvested with 0.25% trypsin/EDTA and washed with cold PBS once. Cells were incubated in 100 μL 1° antibody at in PBS containing 3% bovine serum albumin (BSA) solution for 1 hour at room temperature. Sca-1 and FSP-1 1° and all 2° antibodies were purchased from Abcam (Cambridge, Mass.). Cells were then centrifuged at 800 rpm for 5 min and washed once with cold PBS. Sequentially, cells were incubated in 100 μL FITC-labeled 2° antibody solution at in PBS containing 3% BSA for 30 minutes at room temperature in the dark. After washing with cold PBS, cells were suspended in 20 μL cold PBS and smeared on the slides and allowed to air dry. The slides were mounted with anti-fade mounting medium with DAPI (Vector Laboratories, Burlingame, Calif.) and observed under fluorescent microcopy (Leica CTR6500, Leica Microsystems, Bannockburn, Ill.).

Figure 16:
FIG. 16 shows that the combination treatment with EGF and TGF-β1 induces fibroblast differentiation. Passage 8 murine BMSCs were cultured in IMDM media containing TGF-β1 (10 ng/mL) (Panel A), EGF (10 ng/mL) (Panel B), or TGF-β1 (10 ng/mL) plus EGF (10 ng/mL) (Panel C), for 14 days Immunofluorescence staining was performed using anti-FSP1 antibody.

Immunofluorescence studies confirm that MSCs are differentiated to fibroblasts by EGF and TGF-β1. FIG. 16 illustrates that BMSCs stained positively for FSP1, a fibroblast specific marker, only when treated with the combination of EGF and TGF-β1 (Panel C). No FSP1 staining was observed for BMSCs treated with EGF alone or TGF-β1 alone (Panels A and B). No FSP1 staining was observed for BMSCs treated with bFGF alone or with bFGF and TGF-β1 (data not shown). These data indicate the combination of EGF and TGF-β1 induces fibroblast differentiation.

Example 4

Compositions of Mesenchymal Stem Cell-Derived Fibroblasts

MSCs were grown within a PURAMATRIX™ scaffold according to the manufacturer's protocol (3DM, Cambridge, Mass.). Briefly, MSC were isolated and resuspended at $10^7$ cell/ml in a salt-free iso-osmotic 10% sucrose solution. Equal volumes of PURAMATRIX™ and resuspended cells were mixed and added into 24-well membrane inserts pre-wet in media. For proliferation of MSCs mesenchymal stem cell proliferation media was quickly layered on top of the gel. For differentiation of MSC into fibroblasts, mesenchymal stem cell media may be gently removed and replaced with FDM. To effect MSC proliferation and/or differentiation into fibroblasts on top of the gel, MSC were seeded on top of the PURAMATRIX™ rather than mixed with it.

Figure 12:
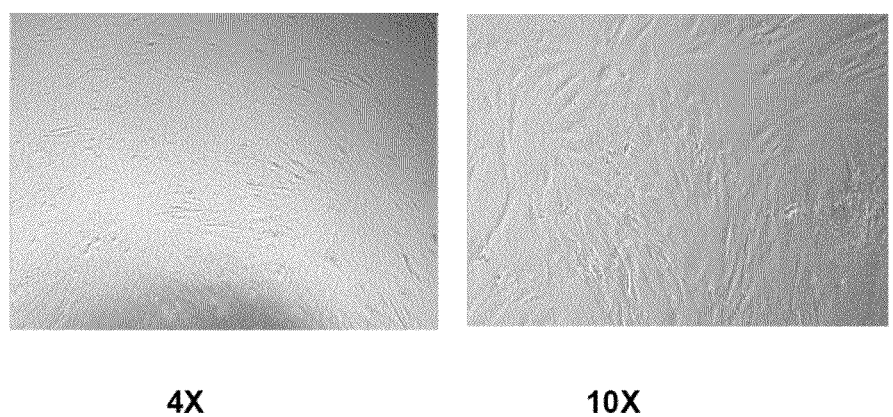
FIG. 12 shows the differentiation of human mesenchymal stem cells in fibroblast differentiating media on top of a self-assembling hydrogel scaffold.
Figure 13:
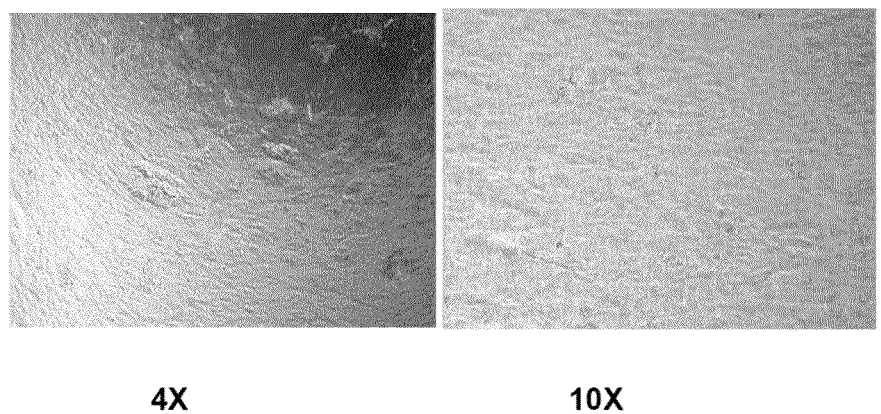
FIG. 13 shows the differentiation of human mesenchymal stem cells in fibroblast differentiating media within a self-assembling hydrogel scaffold.
Figure 14:
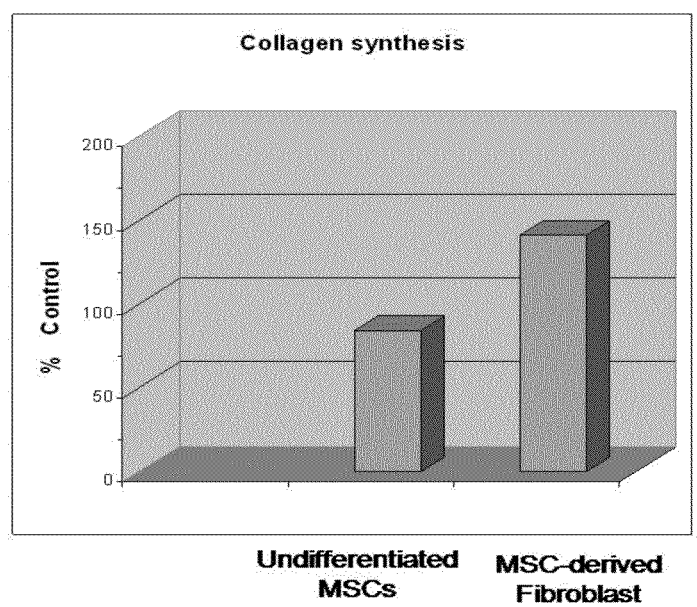
FIG. 14 shows collagen synthesis (% control; y-axis) of mesenchymal stem cells in a hydrogel (undifferentiated MSC) or mesenchymal stem cells differentiated into fibroblasts with EGF and TGF-β1 in a hydrogel (MSC-derived fibroblast).

FIG. 12 shows that MSC-derived fibroblast spread out and grow in a similar fashion as they do in tissue culture treated plastic plates when seeded on top of a scaffold, e.g., MSC derived fibroblasts can grow and be cultured on top of a scaffold. FIG. 13 shows that MSC-derived fibroblasts may be incorporated within scaffold and grow and be cultured while embedded in the scaffold. As shown in FIG. 14, undifferentiated MSCs do not spontaneously differentiate into fibroblasts despite being in the presence of a scaffold. This is evidenced by the lack of collagen synthesis relative to control fibroblast levels. However, in the presence of FDM, MSCs differentiate into fibroblasts and produce collagen at a rate greater than that seen in baseline fibroblasts. This proves that MSCs can be induced to differentiate into fibroblasts using FDM and that once differentiated, the fibroblasts are functional.

What is claimed is:
1. A method for differentiating mesenchymal stem cells (MSC) into fibroblasts, the method comprising:
   culturing in vitro a population of MSC in media comprising epidermal growth factor (EGF) and transforming growth factor (TGF)-β1 for a period of time sufficient to detect FSP-1 expression and a decrease in the expression level of OCT-4; and
   isolating cells from culture such that the isolate comprises at least 25% of FSP-1$^+$, OCT-4$^+$ fibroblasts.
2. The method of claim 1, wherein the media does not comprise any growth factors or cytokines besides EGF and TGF-β1.

3. The method of claim 1, further comprising before said culturing step the steps of:
   contacting a population of MSC with an antibody specific for Sca-1; and
   selecting for cells expressing said Sca-1.

4. The method of claim 1, wherein said population of MSC are isolated from adipose tissue.

5. The method of claim 1, wherein said population of MSC are isolated from bone marrow.

6. The method of claim 1, wherein said culturing is with from about 1 pg/ml to about 1 μg/ml EGF and from about 1 pg/ml to about 1 μg/ml transforming growth factor beta.

7. The method of claim 1, further comprising after differentiating mesenchymal stem cells the step of contacting said differentiated mesenchymal stem cells on top of or within a scaffold with epidermal skin cells.

* * * * *